(12) United States Patent
Wang et al.

(10) Patent No.: US 7,283,241 B2
(45) Date of Patent: Oct. 16, 2007

(54) METHOD AND APPARATUS FOR A MICROSCOPE IMAGE SELECTOR

(75) Inventors: Xinghua Wang, Kent, OH (US);
Thomas C. Voigt, Export, PA (US);
David Tuschel, Monroeville, PA (US);
Chenhui Wang, Stow, OH (US);
Patrick J. Treado, Pittsburgh, PA (US)

(73) Assignee: Chemimage Corp., Pittsburgh, PA (US)

( * ) Notice: Subject to any disclaimer, the term of this patent is extended or adjusted under 35 U.S.C. 154(b) by 314 days.

(21) Appl. No.: 11/045,080

(22) Filed: Jan. 31, 2005

(65) Prior Publication Data

US 2006/0170922 A1    Aug. 3, 2006

(51) Int. Cl.
*G01N 21/25* (2006.01)

(52) U.S. Cl. ................ 356/417; 356/303; 356/320; 356/330

(58) Field of Classification Search ............. 356/417, 356/418, 301, 303, 309, 320, 330; 369/216
See application file for complete search history.

(56) References Cited

U.S. PATENT DOCUMENTS

| | | | |
|---|---|---|---|
| 4,030,827 A * | 6/1977 | Delhaye et al. ............ 356/301 |
| 4,648,714 A * | 3/1987 | Benner et al. ............. 356/301 |
| 5,194,912 A | 3/1993 | Batchelder et al. |
| 5,377,003 A | 12/1994 | Lewis et al. |
| 5,377,004 A | 12/1994 | Owen et al. |
| 5,394,499 A | 2/1995 | Ono et al. |
| 5,442,438 A | 8/1995 | Batchelder et al. |
| 5,493,443 A | 2/1996 | Simon et al. |
| 5,528,393 A | 6/1996 | Sharp et al. |
| 5,623,342 A | 4/1997 | Baldwin et al. |
| 5,689,333 A | 11/1997 | Batchelder et al. |
| 5,710,626 A | 1/1998 | O'Rourke et al. |
| 5,862,273 A | 1/1999 | Pelletier |
| 5,866,430 A | 2/1999 | Grow |
| 5,901,261 A | 5/1999 | Wach |
| 5,911,017 A | 6/1999 | Wach et al. |
| 5,943,122 A | 8/1999 | Holmes |
| 5,974,211 A | 10/1999 | Slater |
| 6,002,476 A | 12/1999 | Treado |
| 6,006,001 A | 12/1999 | Alfano et al. |
| 6,088,100 A | 7/2000 | Brenan et al. |
| 6,091,872 A | 7/2000 | Katoot |
| 6,222,970 B1 | 4/2001 | Wach et al. |

(Continued)

*Primary Examiner*—Roy M. Punnoose
(74) *Attorney, Agent, or Firm*—Duane Morris LLP

(57) ABSTRACT

The disclosure generally relates to a multimode imaging apparatus for simultaneously obtaining multiple wavelength-discriminative spectral images of a sample. In one embodiment, the apparatus includes an image selector having a rotator assembly, the rotator assembly housing a first plurality of optical components, the image selector adapted to receive a illuminating photons having a first wavelength and direct the illuminating photons to the sample, the image selector adapted to receive illuminating photons interacted with the sample and selectively direct said interacted photons to one of a plurality of detection sources; a microscope turret housing a second plurality of components, the microscope turret adapted to receive illuminating photons having a second wavelength and direct the photons to the sample; the microscopic turret adapted to receive illuminating photons interacted with the sample and selectively direct said interacted photons to one of a plurality of detection sources; wherein substantially all of the interacted photons are selectively directed one of a plurality of detection sources to form multiple wavelength discriminative spectral images of the sample simultaneously.

34 Claims, 14 Drawing Sheets

Raman Imaging Output: 90% T/ 10% R

Mirror
NIR Imaging Output: 90% T/ 10% R

Mirror
Fluoresence Imaging Output: 90% T/ 10% R

10% R Mirror
Visible Illumination: 50/50 Beam Splitter (VIS)
Fluoresence Illumination: Dichroic Mirror + Excitation Filter + Emission Filter NIR Illumination: 50/50 Beam Splitter
(NIR)

U.S. PATENT DOCUMENTS

| | | |
|---|---|---|
| 6,483,641 B1 | 11/2002 | MacAulay |
| 6,485,413 B1 | 11/2002 | Boppart et al. |
| 6,571,117 B1 | 5/2003 | Marbach |
| 6,697,665 B1 | 2/2004 | Rava et al. |
| 2002/0054431 A1* | 5/2002 | Costales ..................... 359/462 |
| 2004/0156102 A1* | 8/2004 | Boehm et al. ............. 359/388 |

* cited by examiner

A1, A2 is on Bottom Level
A3, A4 is on top Level

METHOD AND APPARATUS FOR A MICROSCOPE IMAGE SELECTOR

The instant application relates to application Ser. No. 11/045,081 filed even date herewith by certain of the inventors named herein, the specification of which is incorporated herein in its entirety for background information.

BACKGROUND

Spectroscopic imaging combines digital imaging and molecular spectroscopy techniques, which can include Raman scattering, fluorescence, photoluminescence, ultraviolet, visible and infrared absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

In general, the sample size determines the choice of image gathering optic. For example, a microscope is typically employed for the analysis of sub micron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, silicon (Si) charge-coupled device (CCD) detectors or CMOS detectors are typically employed with visible wavelength fluorescence and Raman spectroscopic imaging systems, while indium gallium arsenide (InGaAs) FPA detectors are typically employed with near-infrared spectroscopic imaging systems.

Spectroscopic imaging of a sample can be implemented by one of two methods. First, a point-source illumination can be provided on the sample to measure the spectra at each point of the illuminated area. Second, spectra can be collected over the an entire area encompassing the sample simultaneously using an electronically tunable optical imaging filter such as an acousto-optic tunable filter (AOTF) or a liquid crystal tunable filter ("LCTF"). Here, the organic material in such optical filters are actively aligned by applied voltages to produce the desired bandpass and transmission function. The spectra obtained for each pixel of such an image thereby forms a complex data set referred to as a hyperspectral image which contains the intensity values at numerous wavelengths or the wavelength dependence of each pixel element in this image. Simplified imaging methods using Fiber array spectral translators (FAST) or reduced dimensional optical coupling devices can also be used to obtain lower resolution chemical imaging by segmenting pixels of the image for spectral analysis and analysis of the imaged data set and possible recombination for image analysis purposes.

The ability to improve discrimination testing of inks, stains, fibers and cloth as well as to improve visualization of fingerprints and thin layer chromatography plates are critical to the forensic analysis. Similarly, improved discrimination of irregularities, lesions or cellular objects or pathogens in biomedical or pathology applications is also critical. Such testing often requires obtaining the spectrum of a sample at different wavelengths. Conventional spectroscopic devices operate over a limited ranges of wavelength due to the operation ranges of the detectors or tunable filters possible. This enables analysis in the Ultraviolet (UV), visible (VIS), near infrared (NIR), mid infrared (MIR) wavelengths and to some overlapping ranges. These correspond to wavelengths of about 180-380 nm (UV), 380-700 nm (VIS), 700-2500 nm (NIR) and 2500-25000 nm (MIR). Thus, to obtain a comprehensive spectral analysis over a broad range of wavelengths more than one spectroscopic device must be applied. In other words, a first spectral image of the sample is obtained in a first mode followed by a second image of the sample obtained at a second detection mode.

Conventional methods are time-consuming and often impractical where several spectral images are required simultaneously. The sample position and condition may be changed between the first analysis or a later analysis thereby lessening the ability to precisely correlate the spectra obtained at different wavelength ranges. There is a need for a multi-mode imaging device capable of obtaining multiple wavelength-discriminative spectral images of a sample.

SUMMARY OF THE DISCLOSURE

In one embodiment the disclosure relates to a multimode imaging apparatus for simultaneously obtaining multiple wavelength-discriminative spectral images of a sample, the apparatus comprising an image selector having a rotator assembly, the rotator assembly housing a first plurality of optical components, the image selector adapted to receive a illuminating photons having a first wavelength and direct the illuminating photons to the sample, the image selector adapted to receive illuminating photons interacted with the sample and selectively direct said interacted photons to one of a plurality of detection sources; a microscope turret housing a second plurality of components, the microscope turret adapted to receive illuminating photons having a second wavelength and direct the photons to the sample; the microscopic turret adapted to receive illuminating photons interacted with the sample and selectively direct said interacted photons to one of a plurality of detection sources; wherein substantially all of the interacted photons are selectively directed one of a plurality of detection sources to form multiple wavelength discriminative spectral images of the sample simultaneously.

In another embodiment, the disclosure relates to a method for simultaneously providing multiple wavelength-discriminative spectral image of a sample by providing a plurality illuminating photons to the sample, the illuminating photons defining a plurality of wavelengths and interacting with the sample to provide interacted photons having a plurality of wavelengths; receiving the interacted photons at a microscope turret for discriminatively filtering the photons to one of reflect or refract photons as a function of the photon wavelength; the microscopic turret directing the refracted photons to a first imaging device; providing an image selector for receiving the photos reflected by the microscope turret and further discriminatively filtering the received photons to one of a second imaging device or a third imaging device as a function of the photon wavelength; wherein each of said imaging devices receives the wavelength-discriminated photons substantially simultaneously and provides a wavelength-discriminative spectral image of the sample.

In still another embodiment, a method for obtaining different images of a sample by combining wavelength-selective spectral images of the sample simultaneously includes: illuminating the sample with illuminating photons defining a plurality of wavelengths and interacting with the sample to provide interacted photons having a plurality of wavelengths; receiving the interacted photons at a microscope turret and discriminatively filtering the photons to one of reflect or refract photons as a function of the photon wavelength; the microscopic turret directing the refracted photons to a first imaging device; receiving the reflected photons at an image selector and discriminatively directing the received photons to one of a second imaging device or a third imaging device as a function of the photon wavelength; wherein each of said imaging devices receives the wavelength-discriminated photons substantially simultaneously and provides a wavelength-discriminative spectral image of the sample.

DETAILED DESCRIPTION

Figure 1:
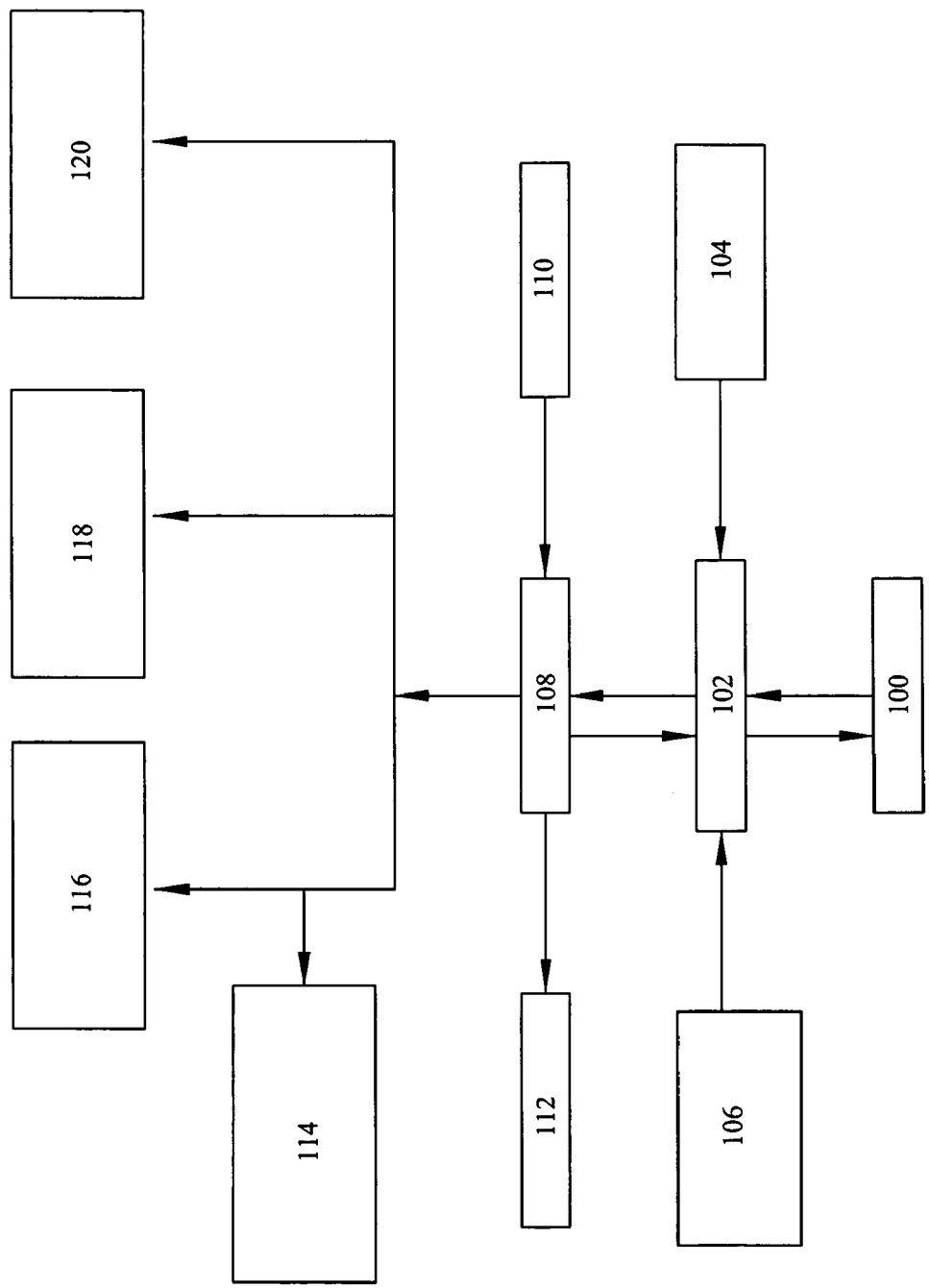
FIG. 1 schematically represents a functional configuration of a multimode image selector according to one embodiment of the disclosure.

FIG. 1 schematically represents a functional configuration of a multimode image selector according to one embodiment of the disclosure. Referring to FIG. 1, sample 100 is positioned below microscope platform 102 which can comprise an optical train, a microscope objective lens or any conventional optical device adapted to communicate photons with the sample. Microscope platform 102 may also include fluorescence/NIR illuminator 104 and/or visible transmissive illuminator 106. In one embodiment, microscope platform 102 receives illuminating photons from at least one of a transmissive illuminator or a fluorescence/NIR illuminator without being directly coupled or integrated therewith.

Illuminating photons communicated to sample 100, interact with sample 100 and form interacted photons. The interacted photons can be collected by microscope turret 102 and directed to images selector 108 for further processing. Illumination sources 104 and 106 are in optical communication with the sample through microscope turret 102. The illumination sources can be integrated with the multimode imaging device or can be optically coupled thereto. Illumination sources 104 and 106 can be selected to provide NIR, VIS or photons of any other desired wavelength.

As shown in FIG. 1, image selector 108 communicates with both Raman illuminator 110 and video imaging device 112. Raman illuminator 110 provides an additional source of illuminating photons to sample 100 thereby enabling simultaneous imaging of the sample with at least three different detection modes. Video imaging apparatus 112 communicates with image selector 108 to record the spectroscopic images of the sample. Video imaging apparatus 112 may include conventional magnetic recording devices.

The system shown in FIG. 1 my optionally include imaging devices 114, 116, 118 and 120, corresponding to dispersive Raman spectroscopy, wide-field Raman imaging, NIR imaging, and Fluorescence imaging, respectively. Each device is adapted to record and communicate a wavelength-discriminative spectrum of the sample. Each optional device may include an ON/OFF select switch to enable the operator to selectively include the desired spectra. More importantly, each device is adapted to cooperate with image selector 108 and microscope platform 102 simultaneously to provide a multiple wavelength-discriminative spectral images of a sample.

Depending on the various combinations, the configuration of FIG. 1 enables implementing the following imaging modes simultaneously: Video Bright Field Transmission (BFT), Video Bright Field Reflectance (BFR), Video Polarized Light Reflectance (PLMR), Video DIC reflectance (DIC), Hoffman Modulation Contrast, Video Polarized Light Transmission (PLMT), Raman dispersive (532 nm excitation, Green Raman), Raman dispersive and Video BFR, Raman Imaging, Raman Imaging and Video BFR, Raman Imaging and Raman Dispersive, Fluorescence Imaging, Fluorescence and Video BFR, NIR Imaging, and NIR Imaging and Video BFR. Thus, by illuminating the sample with photons of various wavelength, in one embodiment the disclosure enables obtaining different chemical spectra simultaneously. The selection of the appropriate illuminating wavelengths is discussed extensively in the co-pending application Ser. No. 11/045,081 filed concurrently herewith, the specification of which is incorporated herein for background information.

Figure 2:
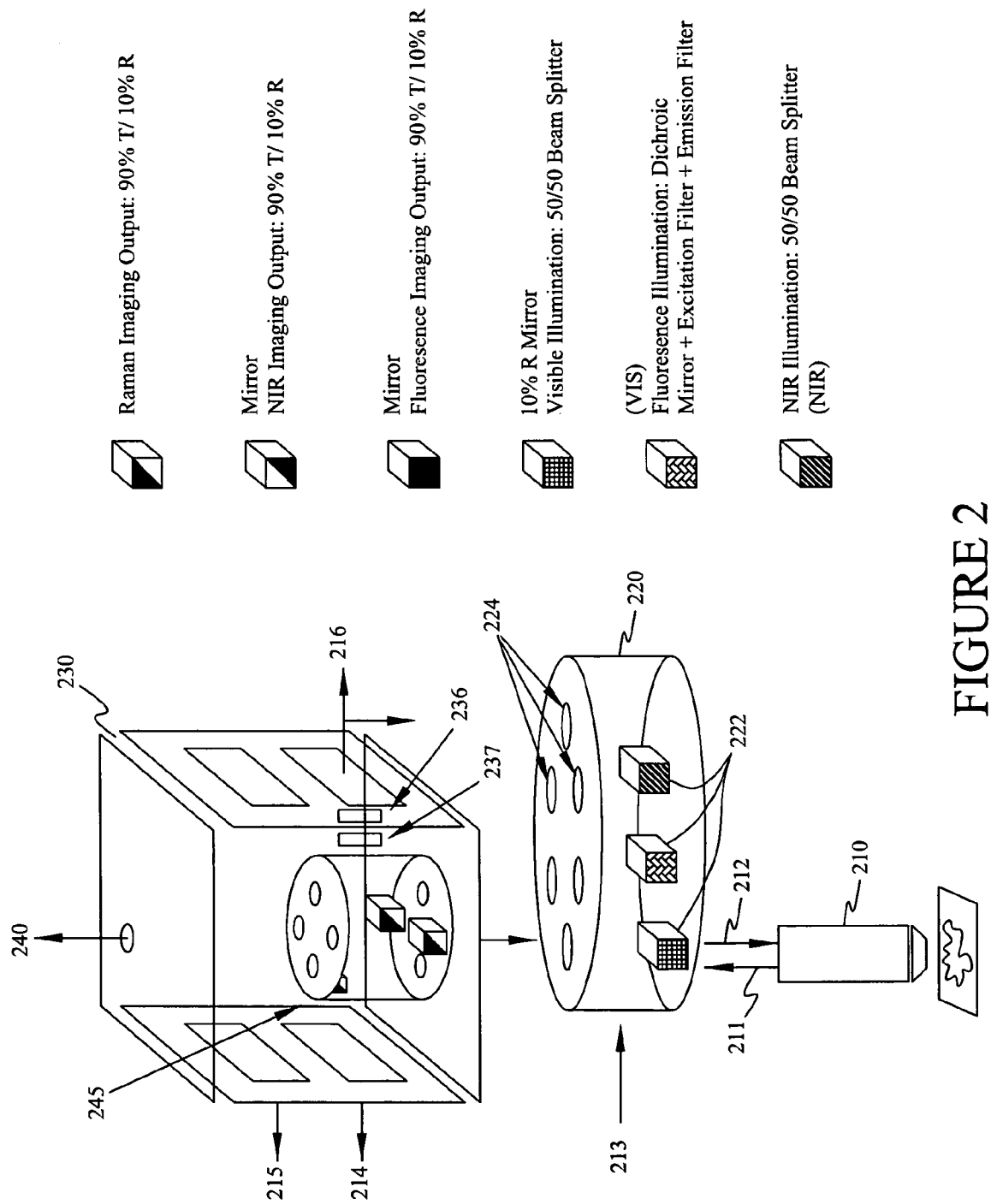
FIG. 2 is a schematic representation of an exemplary apparatus for implementing the functionalities defined in FIG. 1.

FIG. 2 is a schematic representation of an exemplary apparatus for implementing the functionalities defined in FIG. 1. Referring to FIG. 2, microscope objective 210 is optionally interposed between a sample and microscope turret 220. Microscope objective 210 directs illuminating photons 212 received from microscope turret 220 and image selector 230 to the sample. The objective 210 also communicates interacted photons 211 to microscope turret 220, which in—turn selectively directs the interacted photons to one or more imaging device or to image selector 230. The microscope objective may include a microscope objective, a telescope, a macro-optical device, micro-fiber optic bundle and coherent fiber optic bundle. Microscope turret 220 receives one or more of NIR, VIS, or fluorescence illuminating photons and directs the photons to the sample. Illuminating photons can be communicated to the microscope turret through port 213. An exemplary turret 220 may include a plurality of optical elements 222 and a plurality of apertures 224. Aperture 224 may include one or more optical lenses or they maybe empty. Optical elements 222 include dichroic mirror, optical filters (including excitation filter and emission filter), beam splitters, etc. In one embodiment, turret 220 is adapted to selectively match an appropriate optical elements 222 with an appropriate aperture 224.

Photons can be communicated through turret 220 in both direction. That is, illumination photons can be received from image selector 230 and directed 212 to the sample through turret 220; alternatively, interacted photons can be transmitted 211 from the sample to image selector 230 through turret 220. In the exemplary embodiment of FIG. 2, image selector 230 includes a housing and a selector turret 231. Selector turret 231 may include a plurality of apertures 234 and a plurality of optical elements 232. The apertures may include optical lenses and the optical elements include, among others, dichroic mirror, optical filters (including excitation filter and emission filter), beam splitters, etc. Image selector 230 may communicate with imaging devices such as including a video camera, a fluorescence image detection device, a Raman imaging device and a NIR imaging device. Ports 214, 215, 240 and 216 indicate communication with an imaging device. In addition, image selector 230 can receive Raman illuminating photons 245 as well as dispersive Raman illuminating photons 236 and direct said photons to the sample. Image selector 230 is also shown to include a plurality of optical filters 237 for filtering the photons prior to directing the photons to the Raman imaging apparatus. The optical filters may include 7° and 0° filters for removing off-center laser line prior to directing the photons to an imaging device.

To achieve simultaneous NIR and Raman imaging, in one embodiment multiple illumination sources provide light energy (i.e., illuminating photons) simultaneously to the sample. The NIR illumination source generally contains not only NIR spectral of light, but also small amount of visible spectral of light. Such visible spectral of light from the NIR illumination source, generally is much more intense than the Raman scattered signal, which is also in the visible spectral range. The visible spectra of light from the NIR light source can overwhelm the Raman signal and prevent the collection of Raman signal from the sample. Alternatively, it can reduced the signal-to-noise ratio of the collected Raman signal. Consequently, it is important for simultaneous imaging system to include a light source that outputs only the desired spectral range. This can be implemented by several means. For example, a dichroic filter (or similar cutoff filters) can be placed at the output of the light source to reject the unwanted spectra from entering the imaging system. An exemplary illustration of this technique is provided in FIG. 12.

At the same time, the CCD camera used for collecting Raman signal has some sensitivity in NIR spectral range. It is important to reject any unwanted NIR signal to reach the CCD camera that are used for collecting Raman signal. There are many ways to do that, and one example is to place a NIR rejection filter in front of the visible CCD to filter out unwanted spectra from entering the camera. The same considerations apply to situations where simultaneous NIR and Fluorescence imaging or simultaneous Fluorescence and Raman imaging are desired. The illumination sources can be limited to producing only the desired spectra. Otherwise, rejection filter(s) at the output of the illumination can be used. For any imaging device, like a CCD or InGaAs camera, band rejection filter can be used to improve the signal-to-noise ratio of the collected optical signal.

Figure 3A:
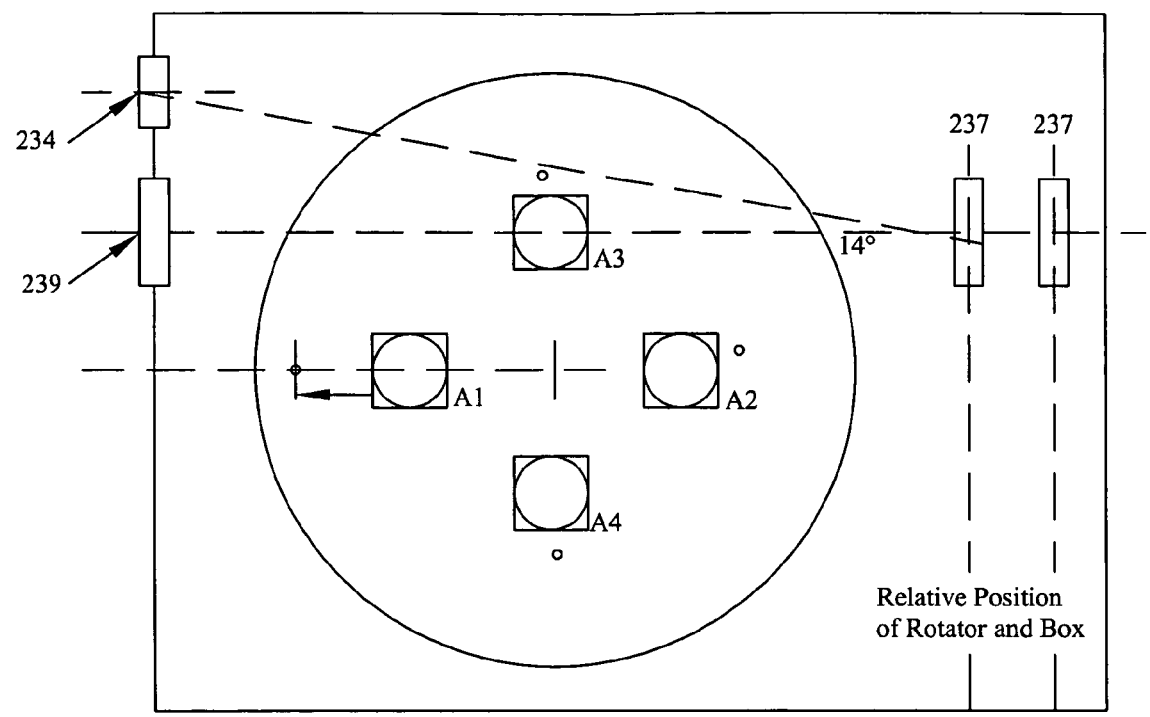
FIG. 3A is a top-view of selector turret as shown in FIG. 2.

FIG. 3A is a top-view of selector turret 231 shown in FIG. 2. As shown, selector turret includes 4 apertures: A1, A2, A3 and A4. Apertures A1 and A2 are on the upper level of turret 231 and apertures A3 and A4 are on the lower level (see FIG. 13B). In addition, filters 237 are positioned to receive laser injection 234 (providing Raman illumination) and direct the illuminating laser photons to the sample. In addition, filters 237 may also receive interacted photons from the sample and direct said photons to port 239 which may be coupled to NIR, VIS, fluorescence or Raman imaging devices. Table 1 shows the various combination of optical elements that can be mounted on imaging turret of FIG. 2 to accomplish simultaneous multi-mode imaging.

TABLE 1

Optical elements mounted on imaging turret of FIGS. 2 and 3A.

| Position | Functionality | Optical Element 232 |
|---|---|---|
| Imaging Turret | | |
| A1 | Raman | 90% T/10% R mirror (for VIS & NIR) |
| A2 | NIR | 90% T/10% R mirror (for VIS & NIR) |
| A3 | Fluorescence | 90% T/10% R mirror (for VIS & NIR) |
| A4 | N/A | |
| Microscope Turret | | |
| B1 | Pass light with no loss | Empty |
| B2 | Visible reflectance illumination. | 50% T/50% R beam splitter |
| B3 | Fluorescence illumination | Dichroic mirror & Excitation Filter & Emission filter |
| B4 | NIR illumination | 50% T/50% R beam splitter (NIR) |
| B5 | N/A | |
| B6 | N/A | |

Figure 3B:
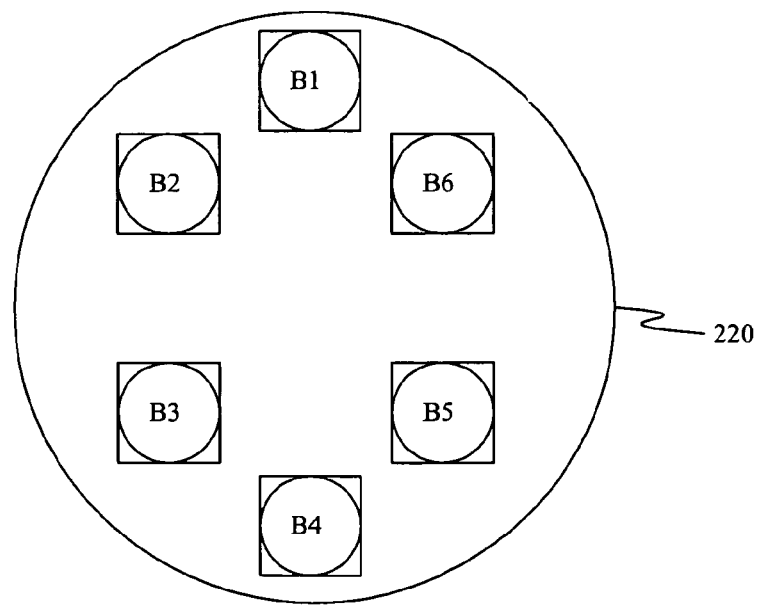
FIG. 3B is a top-view of microscope turret as shown in FIG. 2.

FIG. 3B is a top-view of microscope turret 220 shown in FIG. 2. Microscope turret 220 is shown with 6 apertures 224 numbered B1-B6. As stated, each aperture may receive a different optical lens or a combination of optical lenses. In the illustrated configuration of FIGS. 1, 2 and 3A-B, the optical component for each imaging modes is shown. The detailed optical configuration for different imaging modes will be given in the following illustration. The different imaging modes are supported by selecting a combination of microscope turret position, imaging turret position and one or more illumination sources. The various configurations that can be obtained from the apparatus shown in FIG. 2 is provided in Table 2.

TABLE 2

Summary of optical components and signal loss for different modes of operations of image selector of FIG. 2.

| Imaging Mode | Microscopic Turret position | Element | Illum. Source | Imaging Turret position | Element of Imag. turret | Output port channel | Loss of Signal* |
|---|---|---|---|---|---|---|---|
| Video Modes 1-6 | B2 | 50% T/50% R beam splitter (VIS) | Ram.-Off Halo.-On Mer.-Off | A1, A2, A3, A4 | Any | Video | Video: 50% illumination 50% Signal |
| Raman dispersive and Raman Imaging, Modes 7, 9, 11 | B1 | Empty | Ram.-On Halo.-Off Mer.-Off | A1 | 10% T/90% R mirror (VIS/NIR) | Raman | Raman: 10% on illumination 10% on Signal |
| Raman dispersive or Imaging & Video Modes 8, 10 | B1 | Empty | Ram.-On Halo.-Off Mer.-Off | A1 | 10% T/90% R mirror (VIS/NIR) | Raman/ Video | Raman: 10% on illumination 10% on Signal |
| Fluorescence Imaging Mode 12 | B3 | Dichroic mirror & excitation filter & emission filter | Ram.-Off Halo.-Off Mer.-On | A3 | 10% T/90% R mirror (VIS/NIR) | Fluor. | Fluor.: no loss on illumination 10% on Signal |
| Fluorescence Imaging & Video, Mode 13 | B3 | Dichroic mirror & excitation filter & emission filter | Ram.-Off Halo.-Off Mer.-On | A3 | 10% T/90% R mirror (VIS/NIR) | Fluor. & Video | Fluo: no loss on illumination 10% on Signal |
| NIR Imaging Mode 14 | B4 | 50% T/50% R beam splitter (NIR) | Ram.-Off Halo.-On Mer.-Off | A2 | 10% T/90% R mirror (VIS/NIR) | NIR | NIR: 50% on illumination 55% on Signal |
| NIR & Video Mode 15 | B4 | 50% T/50% R beam splitter (NIR) | Ram.-Off Halo.-On Mer.-Off | A2 | 10% T/90% R mirror (VIS/NIR) | NIR/Video | NIR: 50% on illumination 55% on Signal |

*Expected signal loss excluding loss on DVT and LCTF

Figure 4:
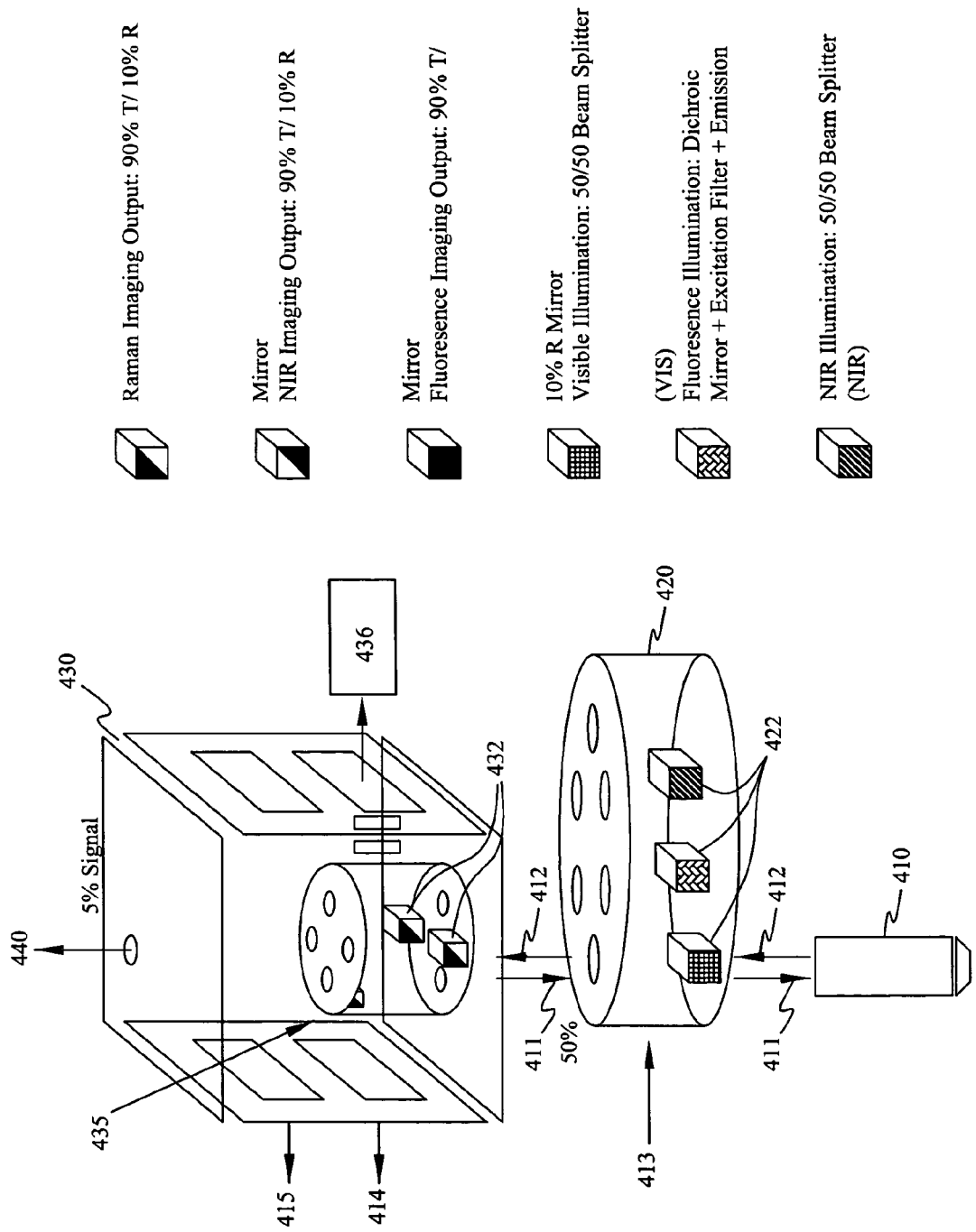
FIG. 4 shows an exemplary optical path through an image selector according to one embodiment of the disclosure.

FIG. 4 shows an exemplary optical path through an image selector according to one embodiment of the disclosure. More specifically, FIG. 4 shows the optical path for imaging modes 1-6 as disclosed in Table 2. In the embodiment of FIG. 2, illumination source 413 provides one or more of NIR, VIS or Fluorescence illumination to microscope turret 420. The turret directs the illuminating photons 411 to the sample though objective lens 410. Optical elements 422 can be selectively used to accomplish the transmission of the photons from illumination source 413 to objective lens 410. Illumination source 413 may include a halogen lamp or a mercury lamp having a wavelength of about 450-700 nm. Upon reaching the sample, the illuminating photons interact with the sample and produce interacted photons. In one embodiment, objective lens 410 may be used to collect the interacted photons and direct the photons to microscope turret 420. Optical elements 422 can then selectively direct the interacted photons to an appropriate imaging device. The step of selectively directing the interacted photons maybe based on the wavelength of the incoming photons such that filters having different wavelength threshold can discriminatively address the interacted photons to the intended imaging device. A controller having a microprocessor with a programmable memory can be used to implement the imaging process and selecting the appropriate illumination sources and configuration of the optical elements.

In the embodiment of FIG. 4, optical elements 422 direct interacted photons 412 through microscope turret 420 to image selector 430. Illumination source 435 can be used to provide be Raman photons directed to the sample as described above. The interacted photons received at image selector 430 can be directed to their appropriate imaging destination, for example, according to their wavelength. Thus, optical elements 432 can discriminately direct the incoming interacted photons to one of fluorescence imaging device 415, NIR imaging device 414 or Raman imaging device 436 (which may include dispersive Raman spectroscopy).

Figure 5:
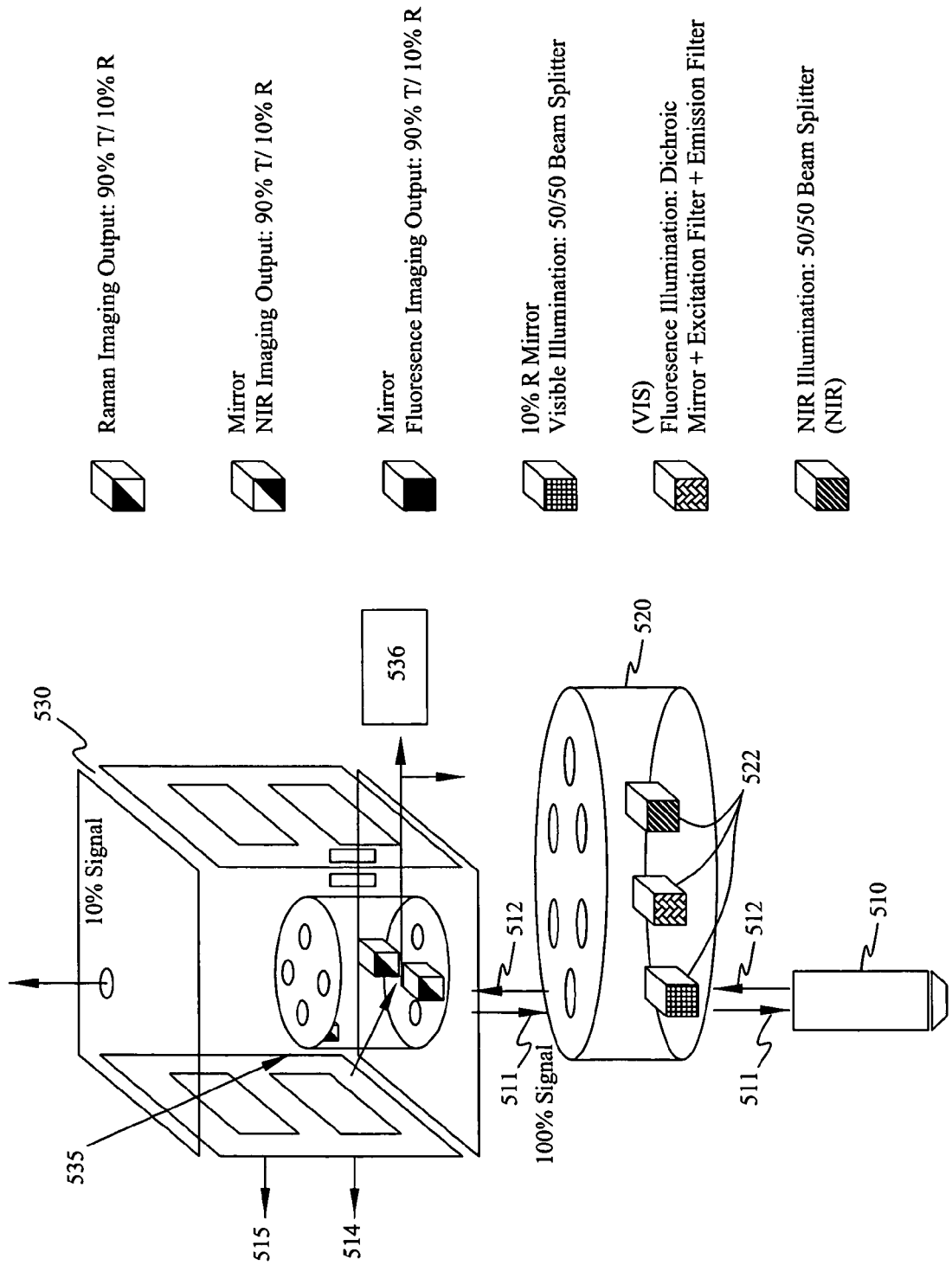
FIG. 5 shows another exemplary optical path through an image selector according to one embodiment of the disclosure.

FIG. 5 shows an exemplary optical path through an image selector according to one embodiment of the disclosure. More specifically, FIG. 5 shows the optical path for imaging modes 7, 9 and 11 as disclosed in Table 2. In the embodiment of FIG. 5, illuminating photons are provided only from Raman illumination source 535. The optical elements is used in this configuration provides about 10% loss on illumination and 10% loss on signal. The imaging modes which can be simultaneously collected are Raman and Raman dispersive.

Figure 6:
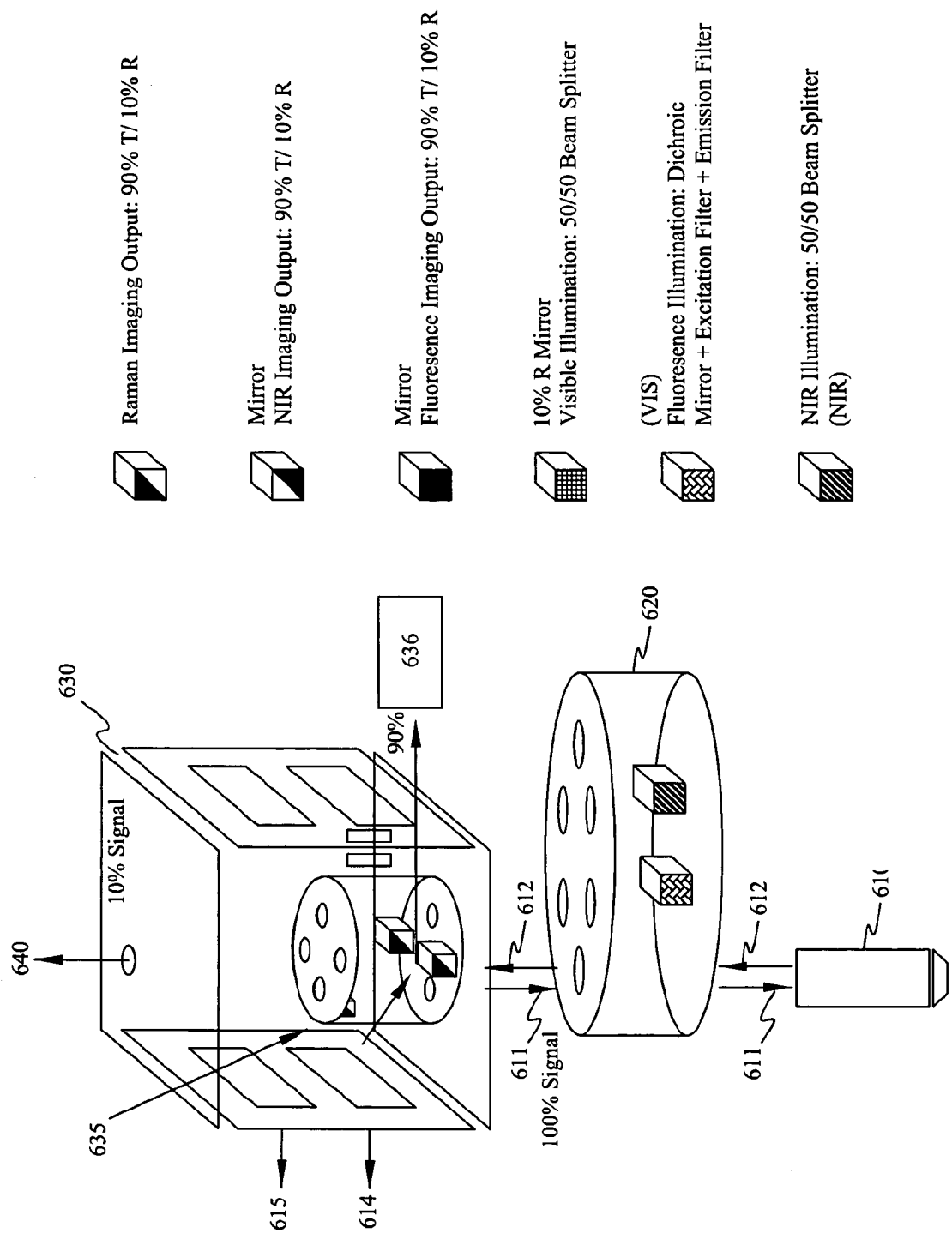
FIG. 6 shows an exemplary optical path through an image selector according to one embodiment of the disclosure.

FIG. 6 shows an exemplary optical path through an image selector according to one embodiment of the disclosure. More specifically, FIG. 6 shows the optical path for imaging modes 8 and 10 as disclosed in Table 2. Here, the only illumination source is the Raman illumination 535. No optical element is used on the microscope turret 520. On the images selector side, optical elements are provided to direct about 10% of the signal to video recording device 640 and about 90% of the signal to DVT 536. Duet Vision Technology, DVT™, (as described in U.S. Pat. No. 6,717,668 entitled "Simultaneous Imaging and Spectroscopy Apparatus" (the specification of which is incorporated herein for background information) allows one of the optical paths of polarized light to be used for dispersive spectroscopy, independent of the use of the light of another polarization in another optical path. The imaging modes which can be simultaneously collected are Raman or Raman dispersive and video imaging.

Figure 7:
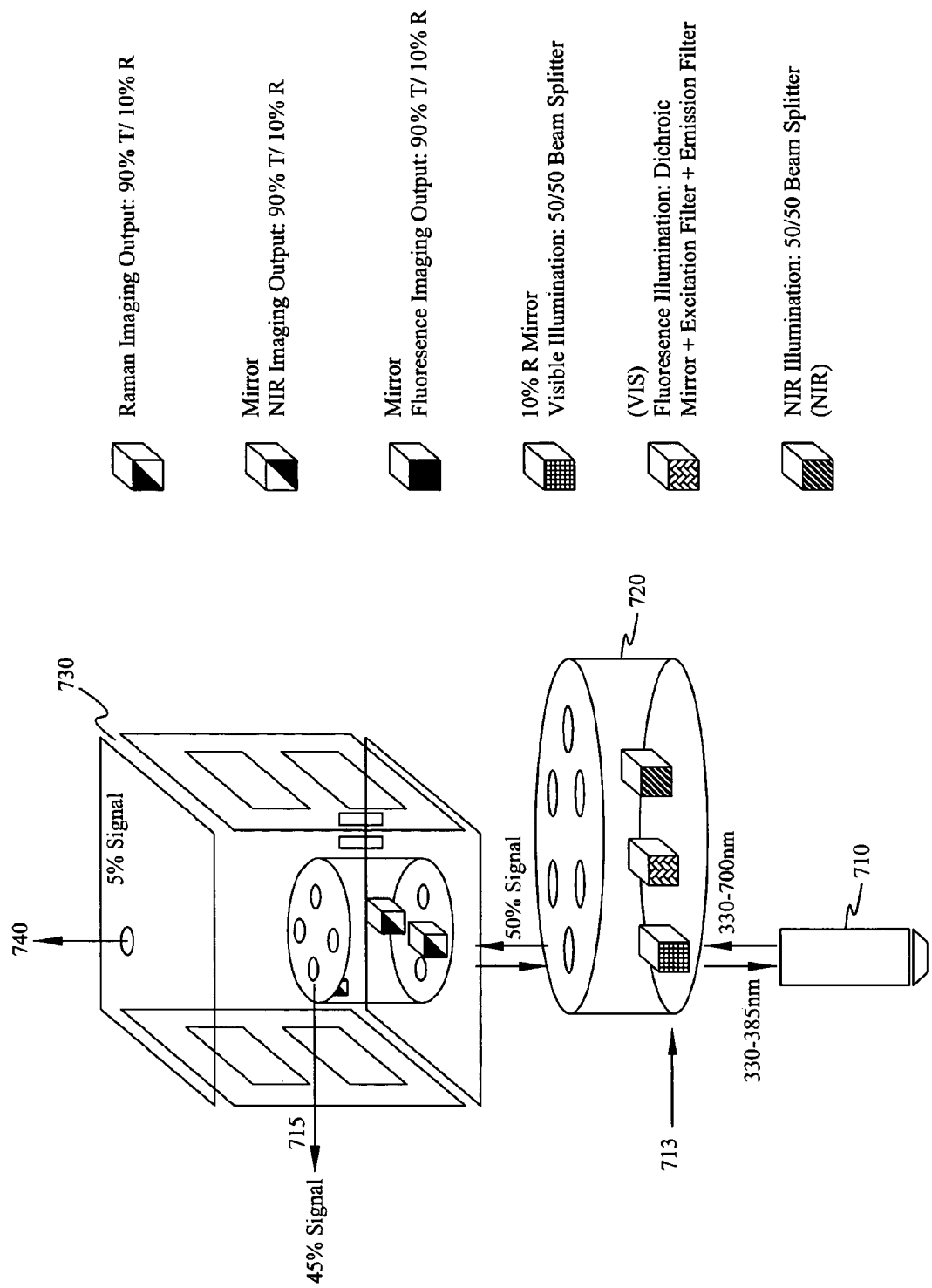
FIG. 7 shows an exemplary optical path through an image selector according to still another embodiment of the disclosure.

FIG. 7 shows an exemplary optical path through an image selector according to still another embodiment of the disclosure. More specifically, FIG. 7 shows the optical path for imaging modes 12 and 13 as disclosed in Table 2. Here, the only illuminating sources is the mercury lamp providing illuminating photons with wavelengths in the range of about 200-550 nm. The activated photons have a wavelength of about 330-700 nm and are directed to the output channels which include fluorescence and video modes. Specifically, about 45% of the signal (i.e., activated photons) are directed to the fluorescence imaging device 715 and about 5% of the signal can be directed to video camera 740. About 50% of the signal is filtered out at the microscope turret.

Figure 8:
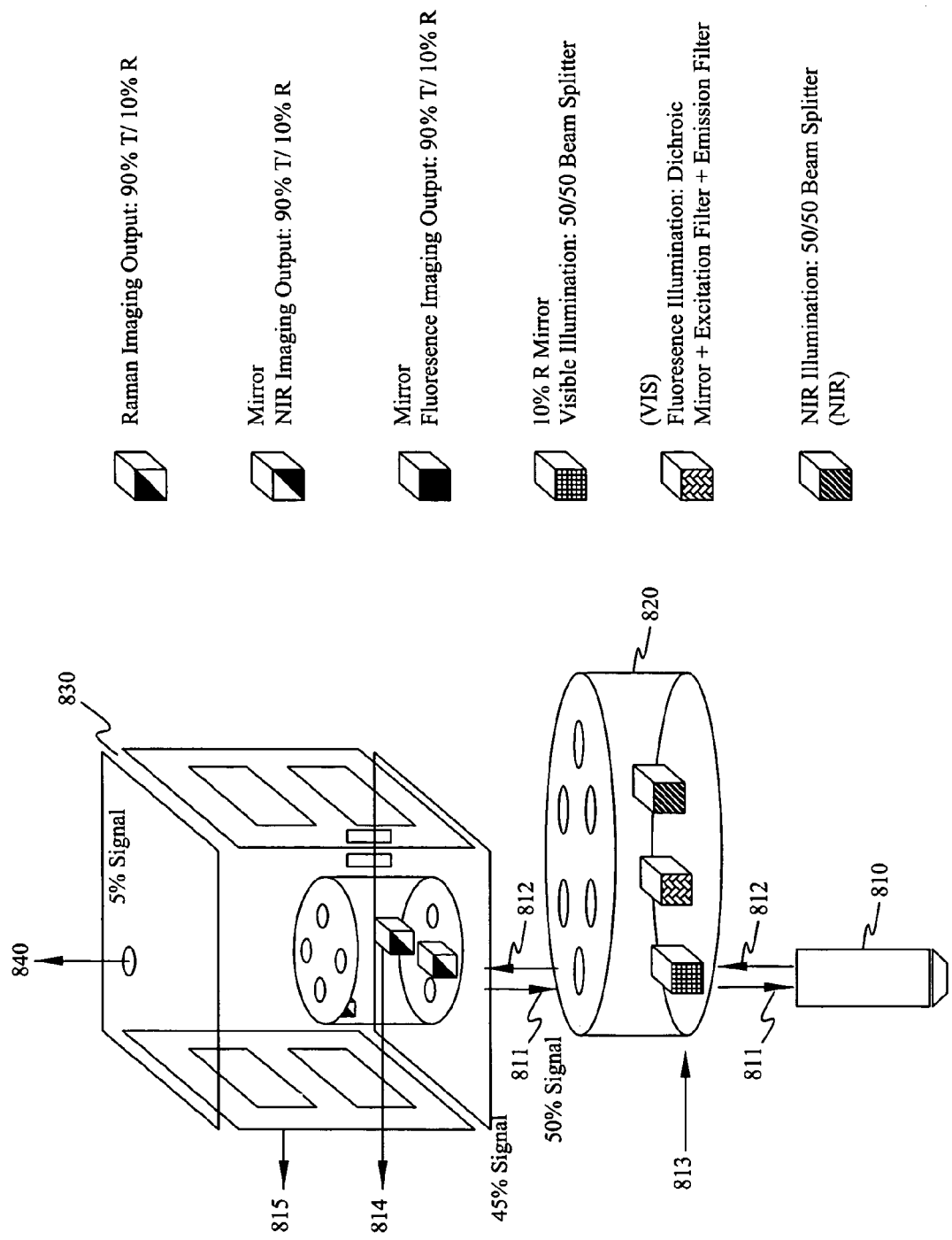
FIG. 8 shows an exemplary optical path through an image selector according to still another embodiment of the disclosure.

FIG. 8 shows an exemplary optical path through an image selector according to still another embodiment of the disclosure. More specifically, FIG. 8 shows the optical path for imaging modes 14 and 15 as disclosed in Table 2. In mode 14, the NIR imaging device 214 is engaged and a halogen lamp positioned at port 813 provides illuminating photons of desired wavelength. A beam splitter having 50% transmission (T)/50% reflection (R) can be used at microscope turret 820 to direct activated photons to image selector 830. At image selector 830 a 10% T/90% R mirror can be used to direct the activated photons to output channel 814, 815 communicating, for example, with NIR imaging device. Similarly, in mode 15, NIR and video images can be obtained from the activated photons simultaneously. In this mode, a 50% T/50% R beam splitter can be used to provide activated photons having suitable wavelength for NIR imaging. The illuminating photons can be provided from halogen lamp source 813. The imaging turret position can be set at A2 to provide a 10% T/90% R mirror and the images can be captured at NIR imaging device and video device 840.

Figure 9:
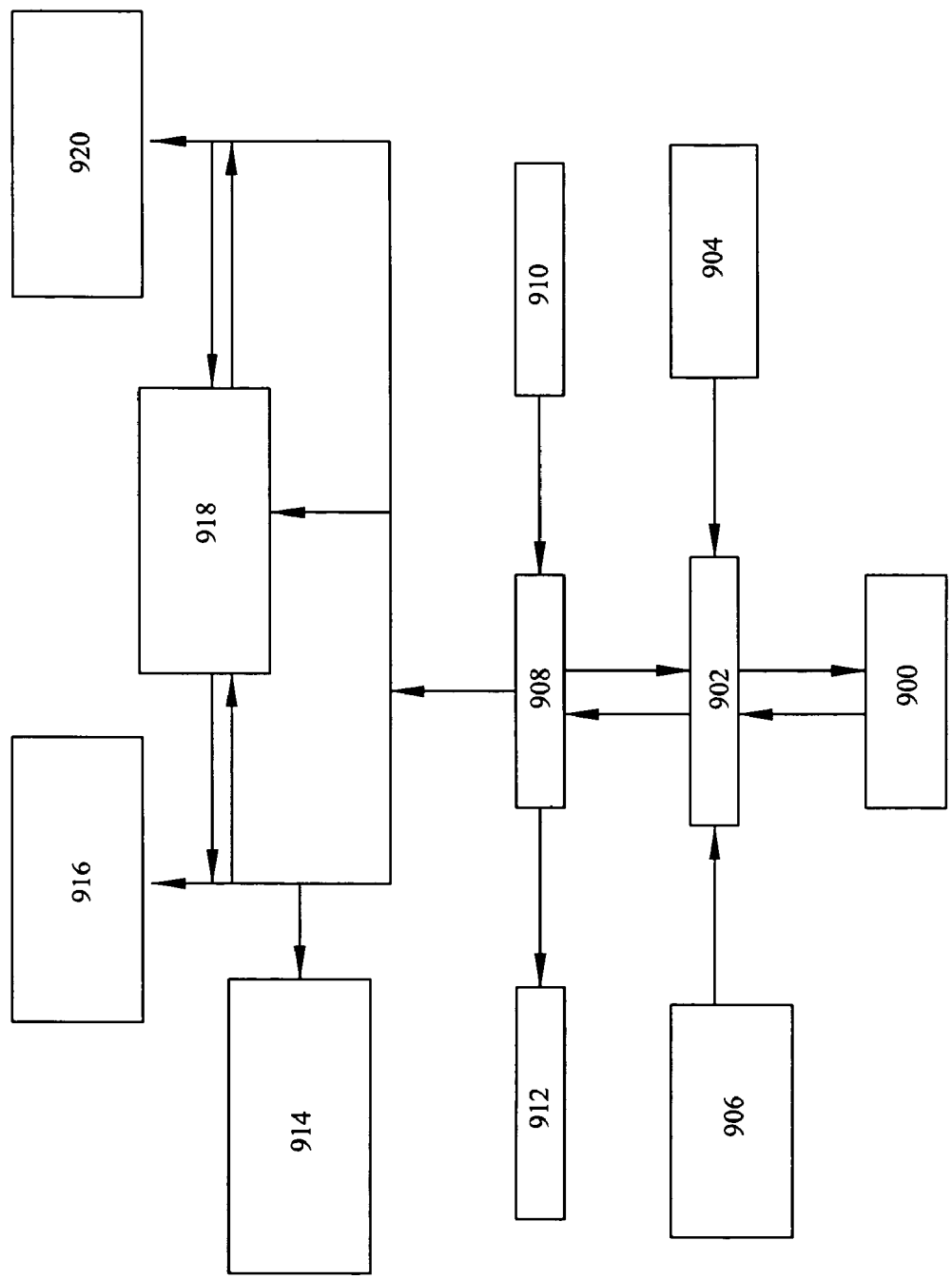
FIG. 9 schematically represents a functional configuration of another multimode image selector according to the principles disclosed herein.

FIG. 9 schematically illustrates a functional configuration of another multimode image selector according to an embodiment of the disclosure. In this configuration, the imaging modes supported by the multimode imaging apparatus include: 1. Video Bright Field Transmission; 2. Video Bright Field Reflectance (BFR); 3. Video Polarized Light Reflectance; 4. Video DIC reflectance; 5. Hoffman Modulation Contrast; 6. Video Polarized Light Transmission; 7. Raman dispersive (e.g., 532 nm excitation, Green Raman); 8. Raman dispersive and Video BFR; 9. Raman Imaging; 10. Raman Imaging and Video BFR; 11. Raman Imaging and Raman Dispersive; 12. Fluorescence Imaging; 13. Fluorescence and Video BFR; 14. NIR Imaging; 15. NIR Imaging and Video BFR; 16. Raman dispersive and NIR Imaging; 17. Raman dispersive, NIR Imaging and Video BFR; 18. Raman Imaging and NIR Imaging; 19. Fluorescence and NIR Imaging; 20. Fluorescence, NIR Imaging and Video.

While the mechanical structure of the image selector remains similar to that of FIG. 2, adding different optical elements to the selector turret or microscope turret can support five new imaging modes. These imaging modes may be simultaneous Fluorescence and Raman or Fluorescence and NIR imaging modes. In this case, the NIR illumination delivery can be changed as compared to the previous image selector configuration.

Referring to FIG. 9, sample 900 optically communicates with the multimode imaging apparatus through the microscope platform 902. The microscope platform may optionally include an objective lens. Visible transmissive illuminator 906 and fluorescence illuminator 904 provide illuminating photons to platform 902. The illumination sources can be integrated with microscope platform 902. Alternatively, the illumination sources can be adapted to optically communicate illuminating photons to microscope platform 902. In the exemplary embodiment of FIG. 9, image selector 908 is communicates with Raman illuminator 910. The Raman illuminator provides Raman photons to the sample. As in the previous configuration, video imaging device 912 is added for recording images. The embodiment of FIG. 9 includes several imaging devices: dispersive video image recording device 912, Raman spectroscopy device 914, wide-field Raman imaging device 916, NIR imaging device 918 and Fluorescence imaging device 920. Each of these imaging devices is optional and can be removed or replaced by another imaging device. Further, the imaging devices can be controlled by a control switch for selective activation.

Figure 10:
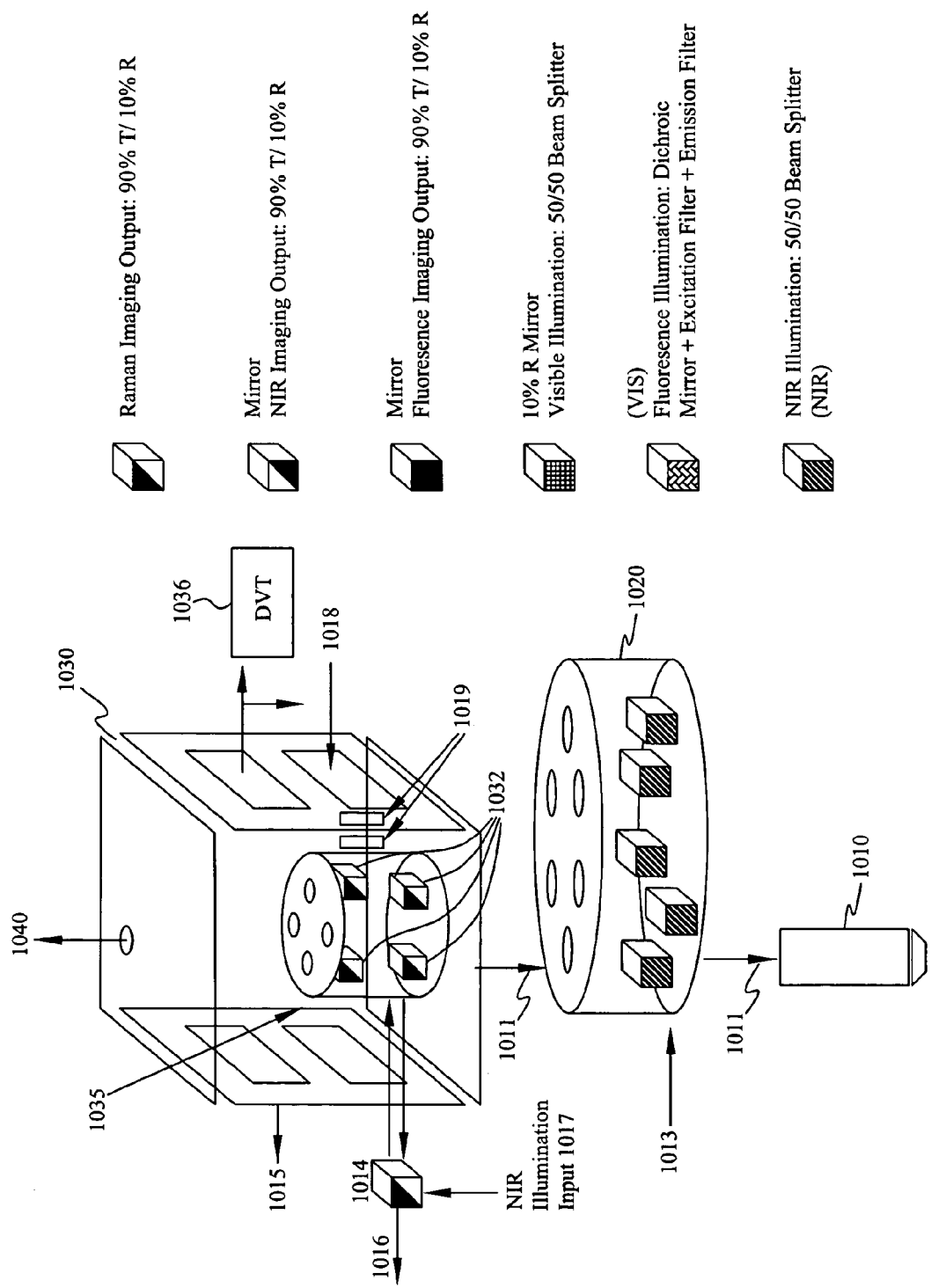
FIG. 10 is a schematic representation of an exemplary apparatus for implementing the configuration defined in FIG. 9.

FIG. 10 is a schematic representation of an exemplary apparatus for implementing the configuration defined in FIG. 9. The embodiment represented in FIG. 10, is adapted to provide simultaneous fluorescence (1013) and NIR or fluorescence and Raman illumination (1035) to the sample. As can be seen from FIG. 10, image selector 1030 includes an image turret with an upper and lower optical elements 1032. As discussed, the optical elements can include one or more of dichroic mirror, optical filters (including excitation filter and emission filter) and beam splitters. In addition to optical elements 1032, optical element 1014 is placed outside of image selector 1030 to communicate illuminating photons 1017 (e.g., NIR) as well as activates photons 1016. Filters (7° and 0°) 1019 are provided to remove undesired laser lines. The filters need not be positioned inside image selector 1030 and can be external thereto. Moreover, filter 1019 need not be similar and can comprise different optical structures or different filters types. A source of dispersive Raman illuminating photons is shown at port 1018. Output ports 1016 and 1015 can be used for NIR imaging and Fluorescence imaging, interchangeably. Output ports 1040 and 1036 can be used for video camera and Raman imaging, interchangeably. The embodiment shown in FIG. 10 may be used to implement the multimode imaging system of FIG. 9. Table 3 shows the optical elements that can be implemented with the exemplary embodiments of FIGS. 9 and 10. Table 4 provides a summary of optical components and signal loss for different modes of operations of image selector of FIG. 10.

TABLE 3

Optical elements for use in the embodiments of FIGS. 9 and 10.

| Position | Functionality | Optical Component 1 (Bottom) | Optical Component 2 (top) |
|---|---|---|---|
| Imaging Turret | | | |
| A1 | Raman/NIR | Dichroic mirror transmits wavelength <800 nm; reflects wavelengths >800 nm. | 90% T/10% R mirror (for VIS & NIR) |
| A2 | N/A | | |
| A3 | Fluorescence/NIR | Dichroic mirror, long pass, transmits wavelength <800 nm; reflects wavelengths >800 nm | 90% T/10% R mirror (for VIS and NIR) |
| A4 | N/A | | |
| Microscope Turret | | | |
| B1 | Pass light with no loss | Empty | Empty |
| B2 | Visible reflectance illumination. | 50% T/50% R beam splitter (VIS) | 50% T/50% R beam splitter (VIS) |
| B3 | Fluorescence illumination | Dichroic mirror and Excitation Filter and Emission filter | Dichroic mirror and Excitation Filter and Emission filter |
| B4 | N/A | | |
| B5 | N/A | | |
| B6 | N/A | | |

TABLE 4

Summary of optical components and signal loss for different modes of operations of image selector of FIG. 10.

| Mode | Micro. Turret position | Element | Illum. Source | Imaging turret position | Element 1 of imaging turret | Element 2 of imaging turret | Output port channel | Loss of Signal* |
|---|---|---|---|---|---|---|---|---|
| 1-6 | B2 | 50%% T/50% R beam splitter (VIS) | Raman Off Halogen On Mercury Off | A1, A2, A3, A4 | Any | Any | Video Camera | Video: 50% illum. 50% Signal |
| 7, 9, 11 | B1 | Empty | Raman On Halogen Off Mercury Off | A1 | Dichroic mirror, long pass >800 nm | 10% T/90% R mirror (VIS/NIR) | Raman | Raman: 10% on illum. 10% on Signal |
| 8, 10 | B1 | Empty | Raman On Halogen Off Mercury Off | A1 | Dichroic mirror, long pass >800 nm | 10% T/90% R mirror (VIS/NIR) | Raman/ Video | Raman: 10% on illum. 10% on Signal |
| 12, 13 | B3 | Dichroic mirror & excitation filter & emission filter | Raman Off Halogen Off Mercury On | A3 | Dichroic mirror, long pass >800 nm | 10% T/90% R mirror (VIS/NIR) | Fluor./ Video | Fluo: no loss on illum. 10% on Signal |
| 14, 15 | B1 | Empty | Raman Off Halogen On Mercury Off | A1, A3 | Dichroic mirror, long pass >800 nm | 10% T/90% R mirror (VIS/NIR) | NIR/ Video | NIR: 50% on illum. 55% on Signal |
| 16, 17, 18 | B1 | Empty | Raman On Halogen On Mercury Off | A1 | Dichroic mirror, long pass >800 nm | 10% T/90% R mirror (VIS/NIR) | NIR/ Raman/ Video | NIR: 50% on illum. 55% on Signal Raman: 10% on illum. 10% on Signal |

TABLE 4-continued

Summary of optical components and signal loss for different modes of operations of image selector of FIG. 10.

| Mode | Micro. Turret position | Element | Illum. Source | Imaging turret position | Element 1 of imaging turret | Element 2 of imaging turret | Output port channel | Loss of Signal* |
|---|---|---|---|---|---|---|---|---|
| 19, 20 | B3 | Dichroic mirror & excitation filter & emission filter | Raman Off Halogen On Mercury On | A3 | Dichroic mirror, long pass >800 nm | 10% T/90% R mirror (VIS/NIR) | NIR/ Fluor./ video | NIR: 50% on illum. 55% on Signal Fluo: no loss on illum. 10% on Signal |

*Expected signal loss excluding

Figure 11:
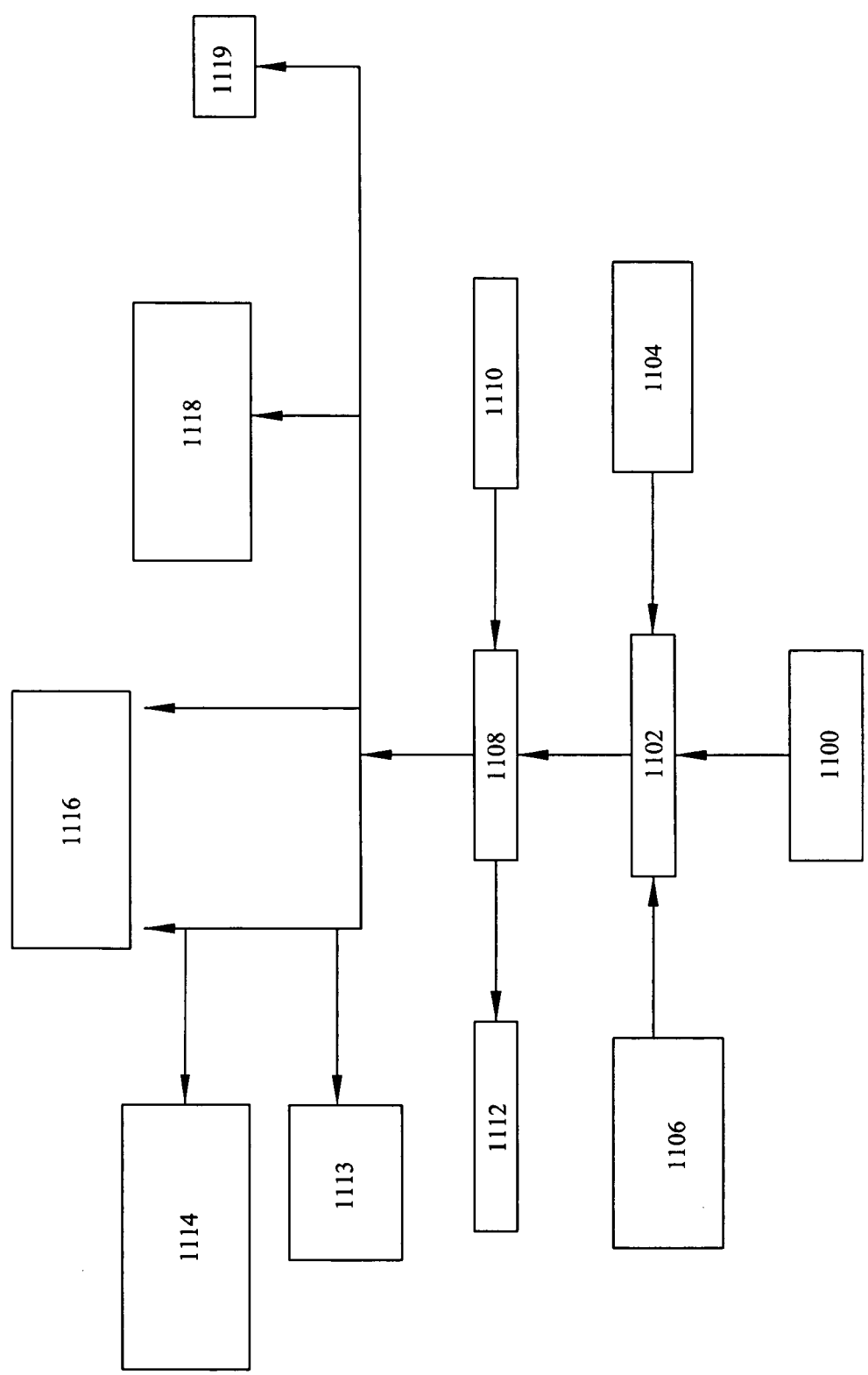
FIG. 11 schematically represents a functional configuration of still another multimode image selector according to the principles disclosed herein.

FIG. 11 schematically represents a functional configuration of still another multimode image selector according to the principles disclosed herein. The imaging modes supported by the multimode imaging apparatus include: 1. Video Bright Field Transmission (BFT); 2. Video Bright Field Reflectance (BFR); 3. Video Polarized Light Reflectance (PLMR); 4. Video DIC reflectance (DIC); 5. Hoffman Modulation Contrast 6. Video Polarized Light Transmission (PLMT); 7. Raman dispersive (785 nm excitation, Red Raman); 8. Raman dispersive and Video BFR; 9. Raman Imaging; 10. Raman Imaging and Video BFR; 11. Raman Imaging & Raman Dispersive; 12. Fluorescence Imaging; 13. Fluorescence and Video BFR; 14. NIR Imaging; 15. NIR Imaging and Video BFR; 16. Raman Imaging (785 nm excitation Red Raman) and Fluorescence Imaging.

In FIG. 11, sample 1100 is positioned below microscope turret 1102. The microscope turret communicates with illumination source 1106, receiving visible transmissive photons. Illuminating source 1104 provides fluorescence illuminating photons. Images selector 1108 receives Raman illuminating photons from illumination source 1110 and communicates activated photons to one or more of video imaging device 1112, fluorescence imaging device 1120, dispersive Raman spectroscopy 1114, wide-field Raman imaging 1116, NIR imaging device 1118. Additional communication ports can be added for additional illumination sources or additional imaging devices. Further, control switches can be incorporates to selectively switch different illuminating sources or imaging devices on or off.

Figure 12:
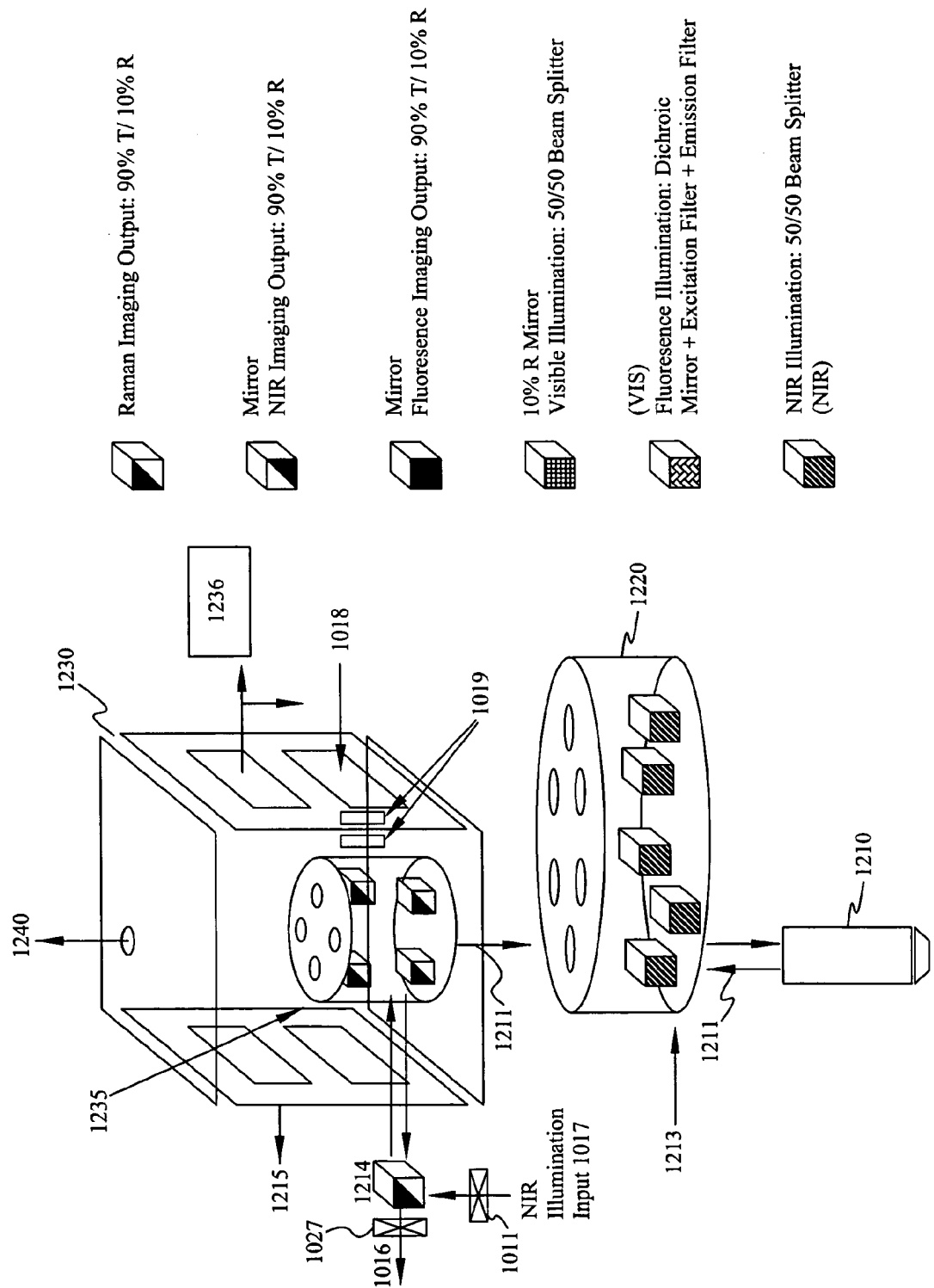
FIG. 12 is a schematic representation of an exemplary apparatus for implementing the configuration defined in FIG. 11.

FIG. 12 is functionally similar to those discussed above. In the embodiment of FIG. 12, optical devices 1011 (e.g., excitation filters) are added to further filter out the unwanted spectra. As discussed, the visible spectra of light from the NIR light source can overwhelm the Raman signal and prevent the collection of Raman signal from the sample. Alternatively, it can reduced the signal-to-noise ratio of the collected Raman signal. To this end, dichroic filter 1011 can be interposed between NIR illumination input 1017 and mirror 1214. Other optical components may be used in place of filter 1011. In an alternative embodiment, an optical component such as filter 1011 may be interposed between the selective imaging device 1230 and the video camera (or CCD) 1240. Additionally, filter 1016 can be positioned after optical component 1214 to further filter unwanted wavelengths. Dichroic filters can be positioned inside or outside images selector 1230 and microscope turret 1220. Other means of implementing the same concept, such as providing an illumination source with a discriminative wavelength output, is within the scope of the disclosure.

Table 5 shows the optical elements that can be implemented with the exemplary embodiments of FIGS. 11 and 12. Table 6 provides a summary of optical components and signal loss for different modes of operations of image selector of FIG. 10.

TABLE 5

Optical elements for use in the embodiments of FIGS. 11 and 12.

| Position | Functionality | Optical Component 1 (Bottom) | Optical Component 2 (top) |
|---|---|---|---|
| Imaging Turret | | | |
| A1 | Raman/Fluor. | Dichroic mirror transmits wavelength >650 nm; reflects wavelengths <650 nm. | 90% T/10% R mirror (for VIS & NIR) |
| A2 | Raman/Video | N/A | 90% T/10% R mirror (VIS & NIR) |
| A3 | NIR | 10% T/90% R mirror (VIS/NIR) | N/A |
| A4 | N/A | | |

TABLE 5-continued

Optical elements for use in the embodiments of FIGS. 11 and 12.

| Position | Functionality | Optical Component 1 (Bottom) | Optical Component 2 (top) |
|---|---|---|---|
| Microscope Turret | | | |
| B1 | Pass light with no loss | Empty | Empty |
| B2 | Visible reflectance illumination. | 50% T/50% R beam splitter (VIS) | 50% T/50% R beam splitter (VIS) |
| B3 | Fluorescence illumination | Dichroic mirror and Excitation Filter and Emission filter | Dichroic mirror and Excitation Filter and Emission filter |

TABLE 6

Summary of optical components and signal loss for different modes of operations of image selector of FIG. 12.

| Mode | Micro. Turret position | Element | Illum. Source | Imaging turret position | Element 1 of imaging turret | Element 2 of imaging turret | Output port channel | Loss of Signal* |
|---|---|---|---|---|---|---|---|---|
| 1-6 | B2 | 50%% T/50% R beam splitter (VIS) | Raman Off Halogen On Mercury Off | A1, A3, A4 | No dichroic | Any | Video Camera | Video: 50% illum. 50% Signal |
| 7, 9, 11 | B1 | N/A | Raman On Halogen Off Mercury Off | A1 | Dichroic mirror, short pass <650 nm | 10% T/90% R mirror (VIS/NIR) | Raman | Raman: 10% on illum. 10% on Signal |
| 8, 10 | B1 | Empty | Raman On Halogen Off Mercury Off | A1 | N/A | 10% T/90% R mirror (VIS/NIR) | Raman/ Video | Raman: 10% on illum. 10% on Signal |
| 12, 13 | B3 | Dichroic mirror & excitation filter & emission filter | Raman Off Halogen Off Mercury On | A1 | Dichroic mirror, long pass >800 nm | 10% T/90% R mirror (VIS/NIR) | Fluor./ Video | Fluo: no loss on illum. 10% on Signal |
| 14, 15 | B4 | N/A | Raman Off Halogen On | A3 | 10% T/ 90% R mirror | N/A | NIR/ Video | NIR: 50% on illum. 55% on Signal |
| 16 | B3 | Dichroic mirror & excitation filter & emission filter | Raman On Halogen Off Mercury On | A1 | Dichroic mirror, long pass >800 nm | 10% T/90% R mirror (VIS/NIR) | Fluo./ Raman/ Video | Fluor.: No loss on illum.; 10% on signal. Raman: 10% on illum. & 10% on signal |

Figure 13A:
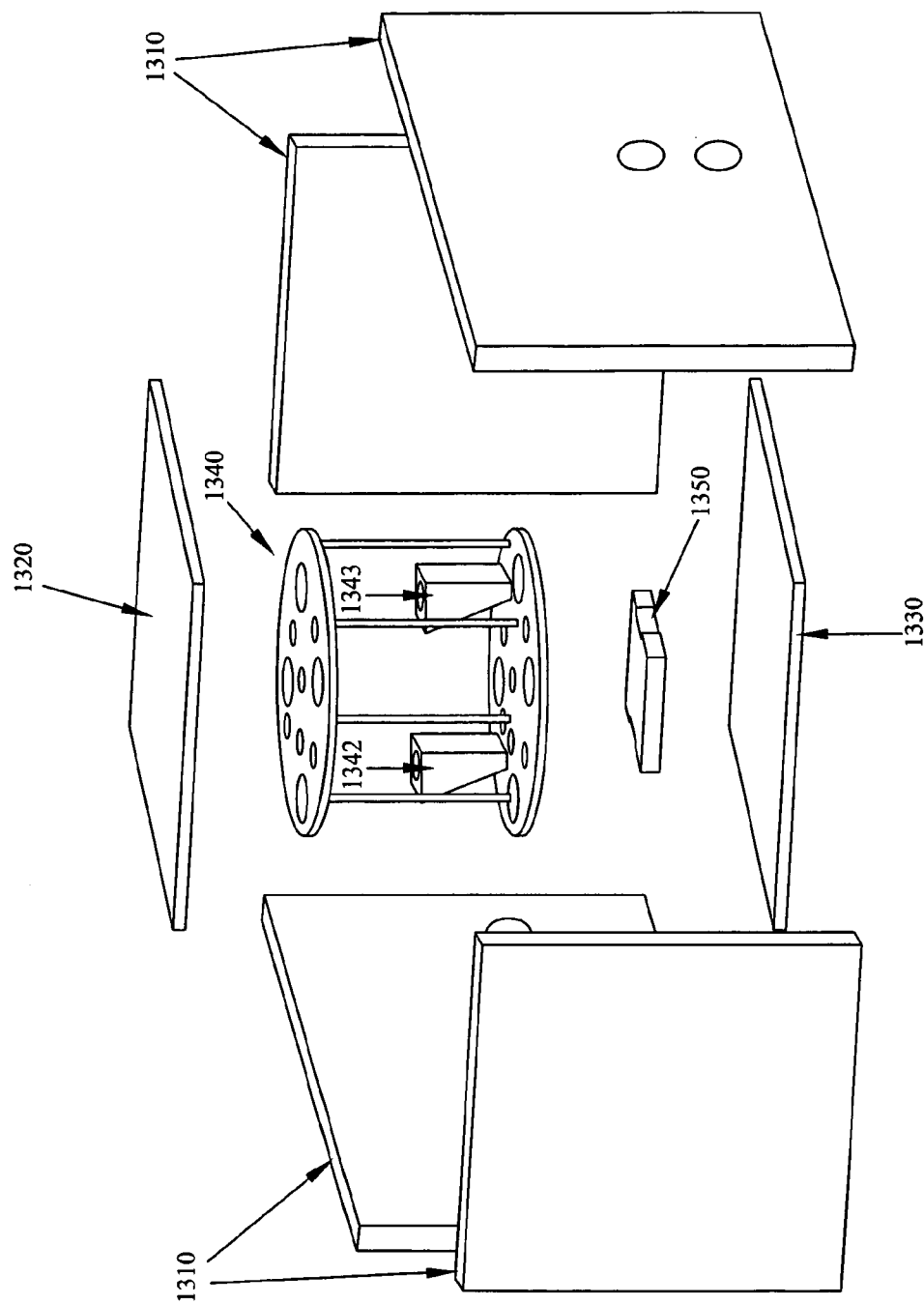
FIG. 13A is a schematic representation of an exemplary image selector.

FIG. 13A is a schematic representation of an exemplary image selector. Image selector 1300 includes housing walls 1310 which receive and enclose imaging turret 1340. The top piece 1320 and bottom piece 1330 include apertures (not shown) for communicating illuminating photons and activated photons to the sample and the imaging devices, respectively. Similarly, apertures 1312 are positioned within walls 1310 to communicate illuminating and activated photons. Imaging turret 1340 is shown with optical elements 1432 and 1342. As stated, the optical elements may include dichroic mirror, optical filters (including excitation filter and emission filter), beam splitters, etc.

Level 1350 is interposed between imaging turret 1340 and the bottom piece 1350 to enable rotational movement of the imaging turret. Bottom piece 1350 can also be used to level imaging turret 1350 with respect to the other component of the multimode apparatus. In one embodiment, the multimode apparatus is devised to selectively match an appropriate optical elements with an appropriate apertures. To this end, imaging turret 1304 can be coupled to a motor or a solenoid to provide rotational motion to the imaging turret. A power transmission and complementary control mechanism maybe used to further control the rotational positioning of the imaging turret.

Figure 13B:
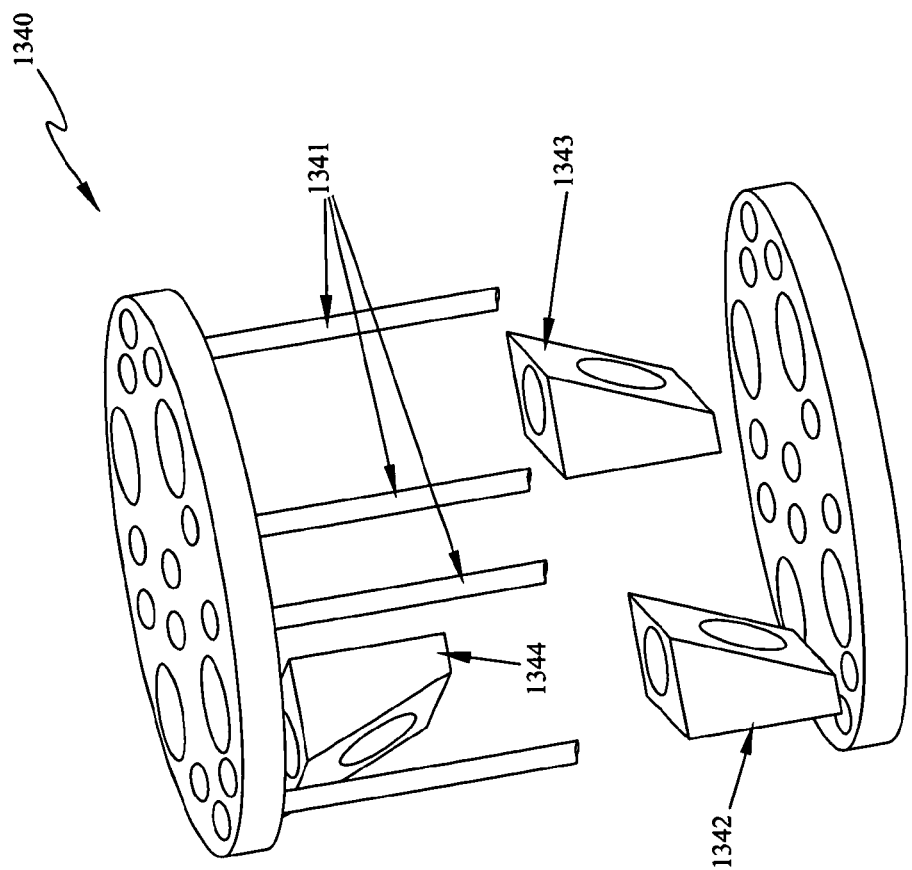
FIG. 13B schematically illustrates an exemplary imaging turret.

FIG. 13B schematically illustrates an exemplary imaging turret. Turret 1340 includes structural columns 1341 and lower optical elements 1343, 1342 as well as an upper optical element 1344. The positioning of optical elements 1344 and 1342 enables simultaneously obtaining additional spectral images of the sample. Imaging turret 1340 as illustrated in FIG. 13B is particularly suitable for the embodiment shown in FIG. 11.

Alignment of the various components and optical elements disclosed herein are a prime consideration. Misalignment error can be contributed from about three different sources. A first source of misalignment error is the tilt error of mounting the mirror in the imaging turret. A second source is the positioning error of the optical elements and the positioning of input/output ports. The third source is the flatness of the mounting bases of the platform (e.g., the turrets and the housing receiving each turret). The misalignment error can contribute a significant error to the optical system and should be eliminated for optimal performance.

The optical elements shown in each of Figures is exemplary and non-limiting. While the principles of the disclosure have been disclosed in relation to specific exemplary embodiments, it is noted that the principles of the invention are not limited thereto and include all modification and variation to the specific embodiments disclosed herein.

What is claimed is:

1. A multimode imaging apparatus for simultaneously obtaining multiple wavelength-discriminative spectral images of a sample, the apparatus comprising:
    an image selector housing a first plurality of optical components, the image selector adapted to receive illuminating photons having a first wavelength and direct the illuminating photons to the sample, the image selector adapted to receive illuminating photons interacted with the sample and selectively direct said interacted photons to one of a plurality of detection sources; and
    a microscope turret housing a second plurality of components, the microscope turret adapted to receive illuminating photons having a second wavelength and direct the photons to the sample; the microscopic turret adapted to receive illuminating photons interacted with the sample and selectively direct said interacted photons to one of a plurality of detection sources;
    wherein substantially all of the interacted photons are selectively directed to one of a plurality of detection sources to form multiple wavelength discriminative spectral images of the sample simultaneously.

2. The apparatus of claim 1, wherein the interacted photons further comprise photons scattered, reflected, refracted, luminescence, fluorescence, Raman scattered, transmitted, absorbed and emitted by the sample.

3. The apparatus of claim 1, further comprising a plurality of illumination sources, each illumination source providing illuminating photons to the sample at a wavelength.

4. The apparatus of claim 3, wherein each illumination source further comprises a diachronic filter for rejecting unwanted wavelength spectrum at the output.

5. The apparatus of claim 3, wherein the illumination source further comprises a fluorescence/NIR illuminator, a visible transmissive illuminator and a Raman illuminator.

6. The apparatus of claim 3, wherein the plurality of illumination sources are coupled to the multimodal system.

7. The apparatus of claim 1, wherein the first plurality of optical components further comprises an optical mirror, a dichroic mirror, an emission filter and an excitation filter.

8. The apparatus of claim 1, wherein the second plurality of components further comprises a beam splitter, a dichroic mirror and an optical filter.

9. The apparatus of claim 1, further comprising a lens selected from the group consisting of a microscope objective, a telescope, a macro-optical device, micro-fiber optic bundle and coherent fiber optic bundle.

10. The apparatus of claim 1, further comprising an acromatic reflective optical assembly.

11. The apparatus of claim 1, further comprising a video camera in communication with the imaging system.

12. The apparatus of claim 11, wherein a dichroic filter is interposed between said video camera and the imaging system to reject unwanted spectrum of wavelength prior to input to the video camera.

13. A method for simultaneously providing multiple wavelength-discriminative spectral image of a sample comprising:
    providing a plurality illuminating photons to the sample, the illuminating photons defining a plurality of wavelengths and interacting with the sample to provide interacted photons having a plurality of wavelengths;
    receiving the interacted photons at a microscope turret for discriminatively filtering the photons to one of reflect or refract photons as a function of the photon wavelength; the microscopic turret directing the refracted photons to a first imaging device;
    providing an image selector for receiving the photons reflected by the microscope turret and further discriminatively filtering the received photons to one of a second imaging device or a third imaging device as a function of the photon wavelength;
    wherein each of said imaging devices receives the wavelength-discriminated photons substantially simultaneously and provides a wavelength-discriminative spectral image of the sample.

14. The method of claim 13, wherein the interacted photons further comprise photons scattered, reflected, refracted, luminescence, fluorescence, Raman scattered, transmitted, absorbed and emitted by the sample.

15. The method of claim 13, further comprising providing a plurality of illumination sources, each illumination source providing illuminating photons at a wavelength.

16. The method of claim 15, further comprising interposing a dichroic filter between the illumination source and the microscope turret or image selector to reject unwanted wavelength spectrum from the illuminating photons.

17. The method of claim 15, the plurality of illumination sources further comprise a fluorescence/NIR illuminator, a visible transmissive illuminator and a Raman illuminator.

18. The method of claim 15, the plurality of illumination sources are coupled to one of the microscopic turret or the image selector.

19. The method of claim 13, wherein the step of discriminatively filtering the interacted photons is implemented by an optical mirror, a dichroic mirror, a beam splitter, an emission filter or an excitation filter.

20. The method of claim 13, wherein the step of providing a plurality illuminating photons to the sample further comprises communicating said illuminating photons to the sample through a microscopic train.

21. The method of claim 13, further comprising a video camera in communication with the imaging system.

22. The method of claim 21, further comprising interposing a dichroic filter between the video camera and the imaging system to reject unwanted spectrum of wavelength prior to input to the video camera.

23. The method of claim 13, wherein the illuminating photons defining a plurality of wavelengths include VIS, NIR, Fluorescent, and Raman wavelengths.

24. A method for obtaining different images of a sample by combining wavelength-selective spectral images of the sample simultaneously, the method comprising:
   illuminating the sample with illuminating photons defining a plurality of wavelengths and interacting with the sample to provide interacted photons having a plurality of wavelengths;
   receiving the interacted photons at a microscope turret and discriminatively filtering the photons to one of reflect or refract photons as a function of the photon wavelength; the microscopic turret directing the refracted photons to a first imaging device;
   receiving the reflected photons at an image selector and discriminatively directing the received photons to one of a second imaging device or a third imaging device as a function of the photon wavelength;
   wherein each of said imaging devices receives the wavelength-discriminated photons substantially simultaneously and provides a wavelength-discriminative spectral image of the sample.

25. The method of claim 24, wherein the interacted photons further comprise photons scattered, reflected, refracted, luminescence, fluorescence, Raman scattered, transmitted, absorbed and emitted by the sample.

26. The method of claim 24, further comprising providing a plurality of illumination sources, each illumination source providing illuminating photons at a wavelength.

27. The method of claim 26, further comprising interposing a dichroic filter between at least one illumination source and the source and the microscope turret or image selector to reject unwanted wavelength spectrum from the illuminating photons.

28. The method of claim 26, wherein the plurality of illumination sources further comprise a fluorescence/NIR illuminator, a visible transmissive illuminator and a Raman illuminator.

29. The method of claim 26, wherein the plurality of illumination sources are coupled to one of the microscopic turret or the image selector.

30. The method of claim 24, wherein the step of discriminatively filtering the interacted photons is implemented by an optical mirror, a dichroic mirror, a beam splitter, an emission filter or an excitation filter.

31. The method of claim 24, wherein the step of providing a plurality illuminating photons to the sample further comprises communicating said illuminating photons to the sample through a microscopic train.

32. The method of claim 24, further comprising a video camera in communication with the imaging system.

33. The method of claim 32, further comprising interposing a dichroic filter to prevent unwanted wavelength spectrum from entering the video camera.

34. The method of claim 24, wherein the illuminating photons defining a plurality of wavelengths include VIS, NIR, Fluorescent, and Raman wavelengths.

* * * * *